United States Patent

Marini

[11] Patent Number: 6,077,290
[45] Date of Patent: Jun. 20, 2000

[54] ENDOSCOPIC INSTRUMENT WITH REMOVABLE FRONT END

[75] Inventor: Louis J. Marini, Abington, Mass.

[73] Assignee: TNCO, Incorporated, Whitman, Mass.

[21] Appl. No.: 09/393,546

[22] Filed: Sep. 10, 1999

[51] Int. Cl.[7] .................................................. A61B 17/00
[52] U.S. Cl. ......................... 606/205; 606/174; 600/564
[58] Field of Search ................................... 606/1, 51, 52, 606/83, 167, 170, 174, 205–210; 600/564–568

[56] References Cited

U.S. PATENT DOCUMENTS

| | | | |
|---|---|---|---|
| 4,674,501 | 6/1987 | Greenberg | 606/174 |
| 5,489,290 | 2/1996 | Furnish | 600/564 |
| 5,571,137 | 11/1996 | Marlow et al. | 606/167 |
| 5,578,052 | 11/1996 | Koros et al. | 606/174 |
| 5,618,303 | 4/1997 | Marlow et al. | . |
| 5,618,308 | 4/1997 | Holmes et al. | . |
| 5,718,714 | 2/1998 | Livneh | . |
| 5,746,759 | 5/1998 | Meade et al. | . |
| 5,782,748 | 7/1998 | Palmer et al. | . |

*Primary Examiner*—Michael Buiz
*Assistant Examiner*—William Lewis
*Attorney, Agent, or Firm*—D. Michael Burns

[57] ABSTRACT

An endoscopic instrument having a ball and socket connection for releasably attaching a front end assembly to an actuating handle assembly comprising of a base having a downwardly extending stationary handle and a pivoting handle. The socket comprising a plurality of resilient prongs to create a friction fit that can be disengaged by the surgeon retracting the pivoting thumb handle. The socket disposed in the base and linkage provided for actuating the instrument.

17 Claims, 8 Drawing Sheets

ENDOSCOPIC INSTRUMENT WITH REMOVABLE FRONT END

BACKGROUND OF THE INVENTION

1. Field of the Invention

The present invention generally relates to surgical instruments, and more particularly to an endoscopic instrument having improved means for removably connecting the actuation rod.

2. Description of the Prior Art

Endoscopic medical procedures for surgery and diagnosis are widely practiced throughout the world today and their acceptance is growing rapidly due to the associated advantages relating to reduced trauma and hospitalization time. These procedures are generally referred to as "minimally invasive surgery". Various types of endoscopic surgical instruments are known in the art. These instruments generally include a slender tube containing a push rod which is axially movable within the tube by means of a manual actuator. One or more end effector mechanisms are coupled to the distal ends of the tube and the push rod so that axial movement of the push rod is translated to rotational or pivotal movement of the end effector mechanisms. End effectors may take the form of scissors, grippers, cutting jaws, forceps, and the like.

Traditionally endoscopic instruments have been manufactured as reusable devices which can be cleaned and sterilized following a procedure, or as disposable devices which are discarded after a single surgical procedure. With disposable devices cleaning is not an issue since they are not reused or resterilized. One of the most common problem is that the end effectors often get dull from use and must be discarded. The end effectors of reusable instruments must always be cleaned and properly sterilized after each surgical procedure. Although techniques such as steam sterilization have been widely used, they are often inadequate to reach all of the blood and tissue residues that can enter an instrument during a surgical procedure. Endoscopic instruments are often constructed with an elongated tubular body housing and small precisioned mechanical parts. Microscopic pockets of blood and tissue, which can infiltrate the body of the endoscopic instrument, are often left on the instrument even after completion of accepted sterilization procedures. Frequently this is because the instrument cannot be adequately disassembled. This creates a concern of infectious disease and the potential of cross-contamination to patients and health care professionals alike. In order to insure complete sterization of a surgical instrument, the instrument must be capable of easy disassembling into its major components. This insures that all surfaces of the instrument are exposed to the particular sterilization medium and any concern that the instrument is not thoroughly sterilized is thereby eliminated.

The advantages of disposable, one time use of these instruments is often compromised by the high cost per instrument and the environmental problems associated with medical waste disposal. The benefits of endoscopic instruments, that are easy to use and which can be assembled and disassembled with a minimum of wasted time due to an economy of parts, have long been recognized. Especially important is an endoscopic instrument having end effector mechanisms which can be easily disconnected for discarding, because it is this part that most often becomes worn, dull and requires the greatest degree of cleaning care.

An example of a surgical instrument that depicts a removable front end is shown in U.S. Pat. No. 5,718,714 issued to Livneh on Feb. 17, 1998. Livneh teaches of a handle assembly having a releasable coupling member which releasably connects with the front end member. The front end member is capable of rotation and the rotation can also be inhibited by a locking member. This patent discloses the advantages from being able to use a variety working front end elements. The proximal end of the front end shaft is seated within a rigid slot. Entrance to the slot is by manually turning a cap assembly that opens up access to the slot therein.

U.S. Pat. No. 5,618,308 issued to Holmes et al., discloses a simple surgical instrument which seats the inner rod within the thumb loop housing by means of a rigid slot. Several steps are required to remove the connecting member from the housing.

U.S. Pat. No. 5,618,303 issued to Marlow et al., discloses a knurled knob for easy rotation of the actuator rod. He also teaches the removal of only the working part of the instrument, This is the part of the instrument that is most likely exposed to contamination and also the hardest to clean. The mechanism for connecting the working end to the shaft can often be almost as difficult to clean as the original working member.

U.S. Pat. Nos. 5,782,748 and 5,746,759 are presented as examples of the prior art seeking to disclose detachable shaft connections.

None of the above inventions and patents, either singly or in combination, is seen to describe the instant invention as claimed.

SUMMARY OF THE INVENTION

Accordingly, the above problems and difficulties are obviated by the present invention which provides for an endoscopic instrument having a removable front end that utilizes a ball and socket connection to a handle housing. The socket connection is relatively flexible, being comprised of a plurality of resilient prongs.

More particularly, the endoscopic surgical instrument of the present invention is comprised of a handle assembly, an elongated endoscopic front end assembly extending from the handle assembly and an end effector mechanism being supported on a distal end of the front end assembly. The end effectors actuate between open and close positions by movement of a pivoting thumb handle which pivots in relation to a stationary finger handle. The end effectors may comprise a pair of jaw members wherein one or both jaw members open and close to perform various endoscopic surgical procedures. The mechanism includes, but is not limited to, scissor devices, dissecting devices, retractor devices, and like mechanisms.

The front end assembly is comprised of a tubular sheath element with a cointensive actuation element coaxially transposed within it, such that it interconnects the handle assembly to the end effectors. The handle assembly mainly comprises a base having the stationary finger handle and the pivotal thumb handle being pivotally connected to each other.

The present invention also includes the provision of a knurled knob on the sheath element for grasping the front end. The front end can be rotated to position the end effectors at various angles to the longitudinal axis during a surgical procedure. The handle assembly has a housing section defined in the base for encasing a socket bushing. The bushing having a socket capable of accepting a spherical end integral with the proximal end of the actuation element. An undercut groove in the sheath element cooperates with a threaded locking knob located in the finger handle to lock into position the front end assembly. The thumb handle controls the engagement of the front end, and makes the instrument suitable for use with disposable front ends.

The surgical instrument of the present invention provides numerous advantages. Because the front end is easily detachable, the handle assembly can be economically cleaned and therefore reusable. Dull and used effector ends can be discarded and replaced with fresh ones. The entire instrument need not be replaced. This provides significant cost savings over devices which must be completely replaced. The instrument is simple to manufacture, and may incorporate any one of a series of end effectors attached to the distal end of the rod for various surgical procedures. Also many moving parts normally associated with such a highly precisioned instrument are eliminated, thus reducing instances of mechanical failure requiring expensive repair or ultimate destruction of the instrument.

The present invention employs a spherical end at the proximal end of the actuation element to plug into a multiple prong flexible socket contained within the upper portion of the stationary handle. The front end is assembled into the handle by the user retracting the locking knob and retacting the thumb handle, then inserting the spherical end into the handle, then tightening the locking knob to secure the front end in place and then closing the thumb handle to engage the spherical end of the actuation element into the socket. The instrument is then ready for use. When desired the front end can be rotated by loosening the locking knob, rotating the front end to desired placement, and then tightening the locking knob.

A primary object of the present invention is to provide a surgical instrument, whereby the front end can be economically discarded upon the cutting members of the end effectors becoming worn or dull from use.

An important object of the present invention is to provide an endoscopic instrument that is inexpensive to manufacture.

Another object of the present invention is to provide a an endoscopic instrument that is easy to assemble and use.

Still another object of the present invention is to provide a means for connecting the actuation element to the handle, which then can be disengaged by the user merely maneuvering the thumb handle and locking knob.

An object of the present invention is to provide an instrument that will have a minimum number of parts requiring sterilization, especially in the handle assembly which is seldom meant to be disposable.

A further object of the invention is to provide an instrument with a front end that will not be inadvertently disengaged during a procedure.

These and other objects of the present invention will become readily apparent upon further review of the following specification and drawings.

BRIEF DESCRIPTION OF THE DRAWINGS

The foregoing objects and other features of the invention will become readily apparent and may be understood by referring to the following detailed description of an illustrative preferred embodiment of the endoscopic surgical instrument having a novel ball and socket connection mechanism for connecting the front end of the instrument to the handle assembly.

DETAILED DESCRIPTION OF THE PREFERRED EMBODIMENT

The endoscopic instrument described herein includes a handle assembly, a removable front end assembly which interconnects the handle assembly to operable end effector mechanisms. The front end assembly includes a tubular sheath element and connector element movable within the sheath. The distal end of the front end assembly may be operably connected to any number of end effectors for actuation of a surgical device. The proximal end of the front end assembly is removably and operably connected to the handle assembly for transmission to the end effector surgical device which is manually manipulated by the surgeon. The novel feature of the instrument is in the manner in which the front end is removably connected to the handle assembly. The benefits derived from the present invention would be equally applicable to laparoscopic instruments.

The description below refers to an endoscopic instrument in accordance with the invention. However, this description is not intended to limit the scope of the present invention, but merely to be illustrative and representative thereof.

Figure 1:
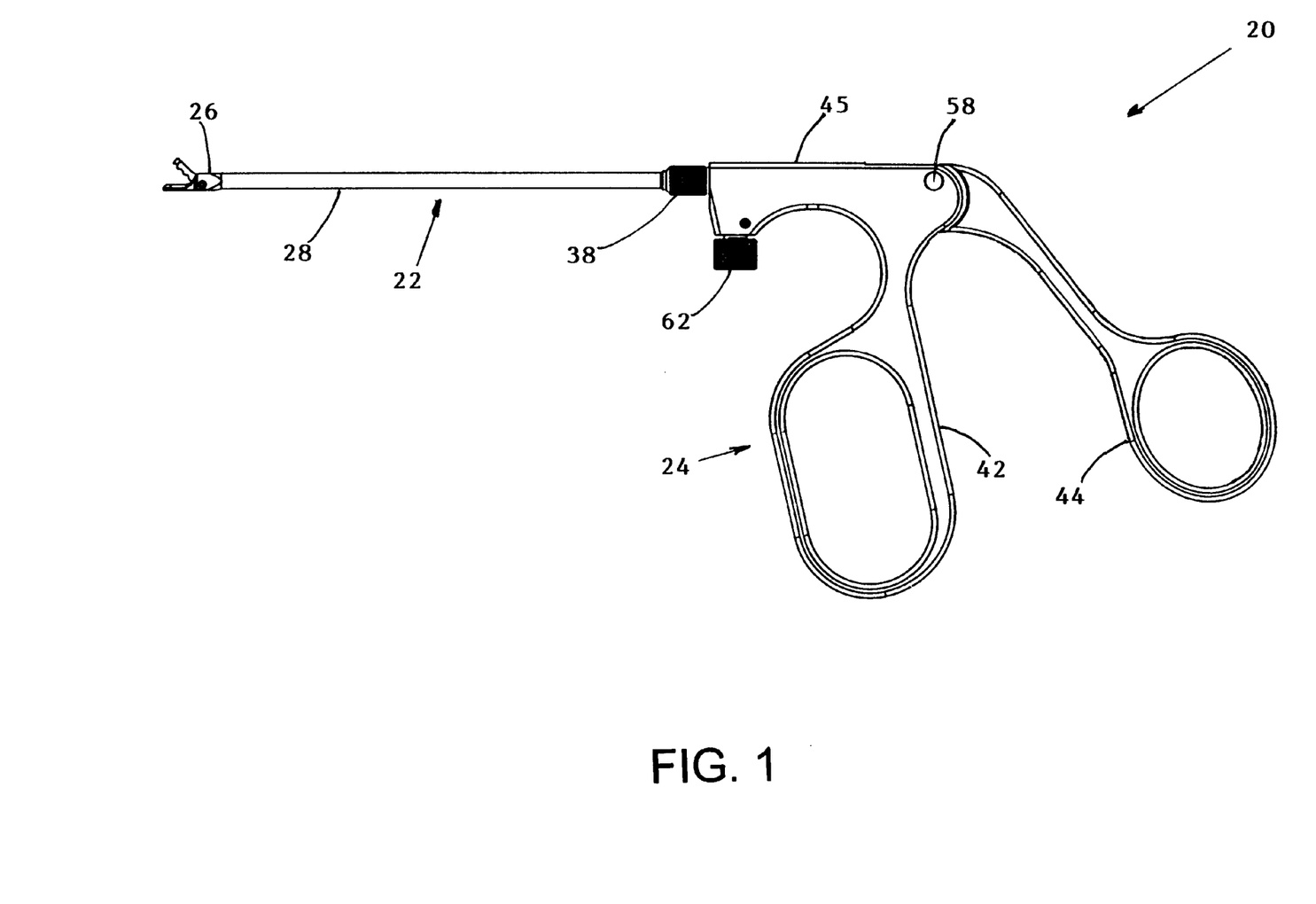
FIG. 1 illustrates a side elevational view of the endoscopic instrument.
Figure 2:
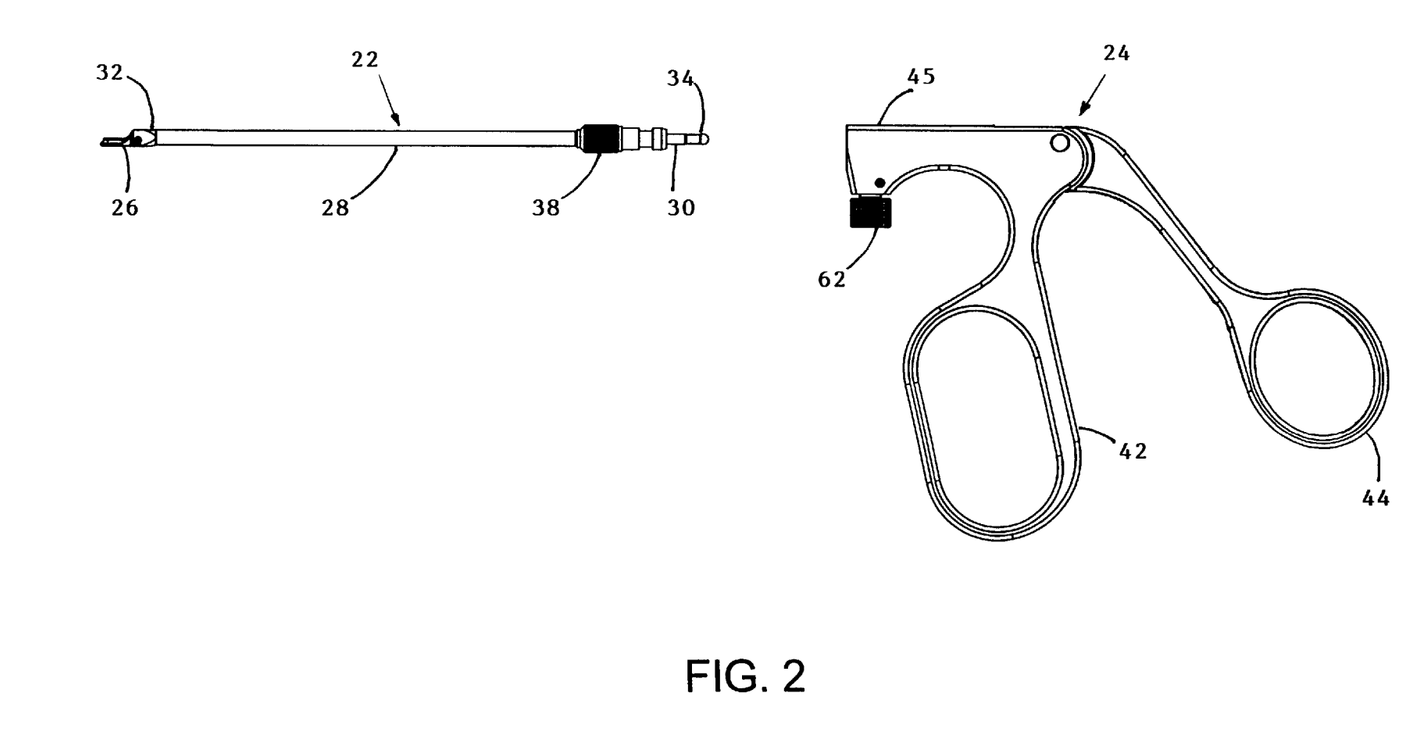
FIG. 2 is an exploded side elevational view of the endoscopic instrument.

Referring now to FIGS. 1 and 2, endoscopic instrument 20 includes a front end assembly 22 and a handle assembly 24 which is operably interconnectable with any linear actuated end effector mechanisms 26 that may be positioned on a distal end 32 of front end assembly 22. Front end assembly 22 includes a tubular sheath element 28 and a rod-shaped actuation element 30 cointensively and coaxially slidably disposed within the sheath 28. Distal end 32 of actuation element 30 is operably connected to end effector 26 for actuation of a surgical device. The proximal end 34 of actuation element 30 having a spherical end 36 for removably engaging with handle assembly 24. For this present invention disclosure the spherical end 36 will be shown as a ball, but it is to be appreciated that other shapes may work as well. A knurled grip 38 is integral with the front end assembly 22 near to the proximal end 34 to assist the surgeon in grasping the front end assembly 22 for purposes of engaging or disengaging it, or to rotate end effector mechanism 26 into a different angle of orientation.

Figure 3:
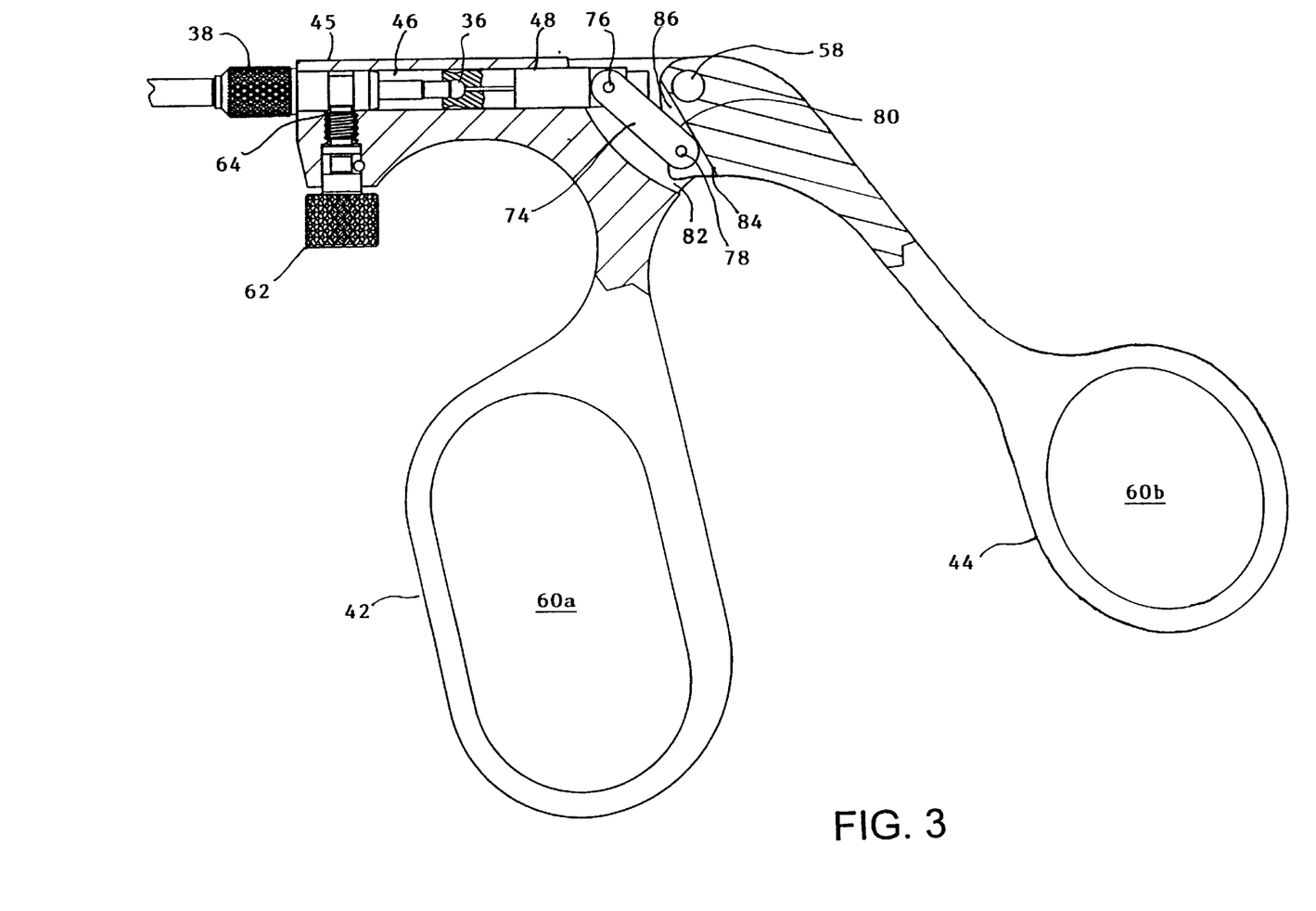
FIG. 3 is a partial cross-section of the handle assembly with the front end assembly engaged therein.
Figure 4:
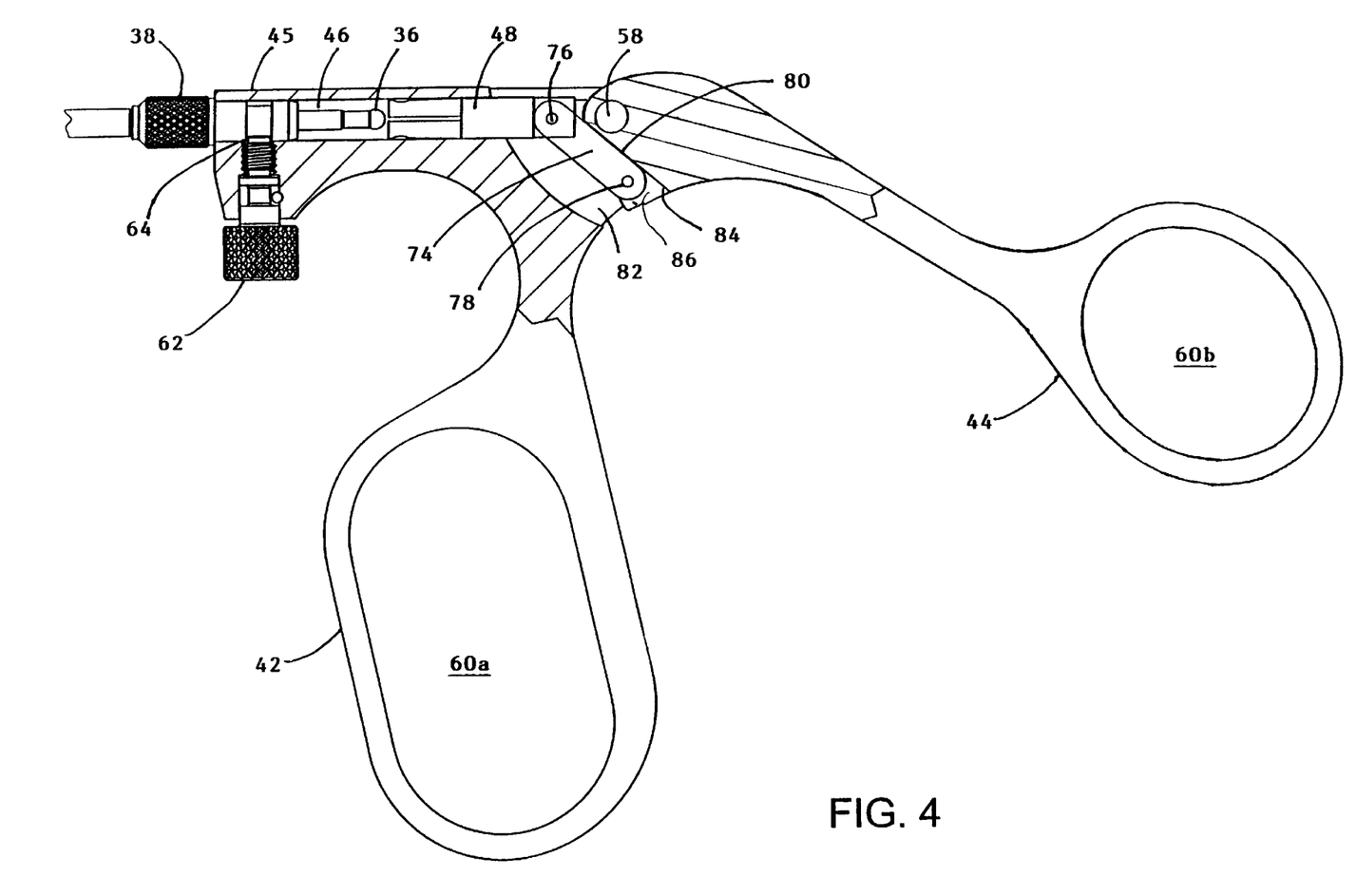
FIG. 4 is a partial cross-section of the handle assembly with the front end assembly disengaged.
Figure 5:
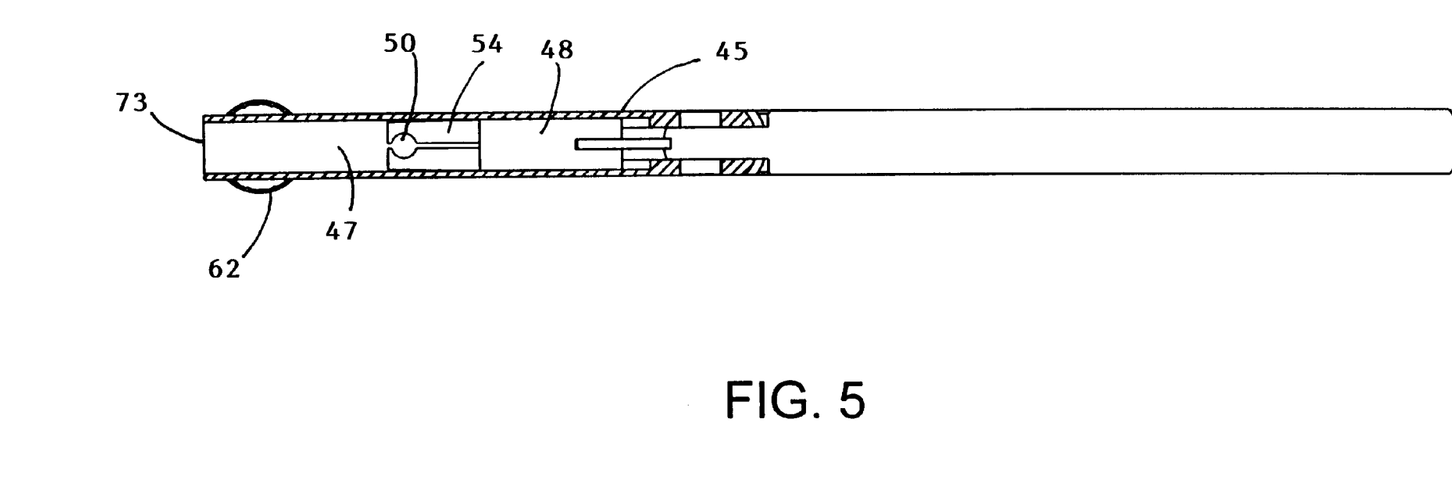
FIG. 5 is a top plan view of the base/handle section.
Figure 6:
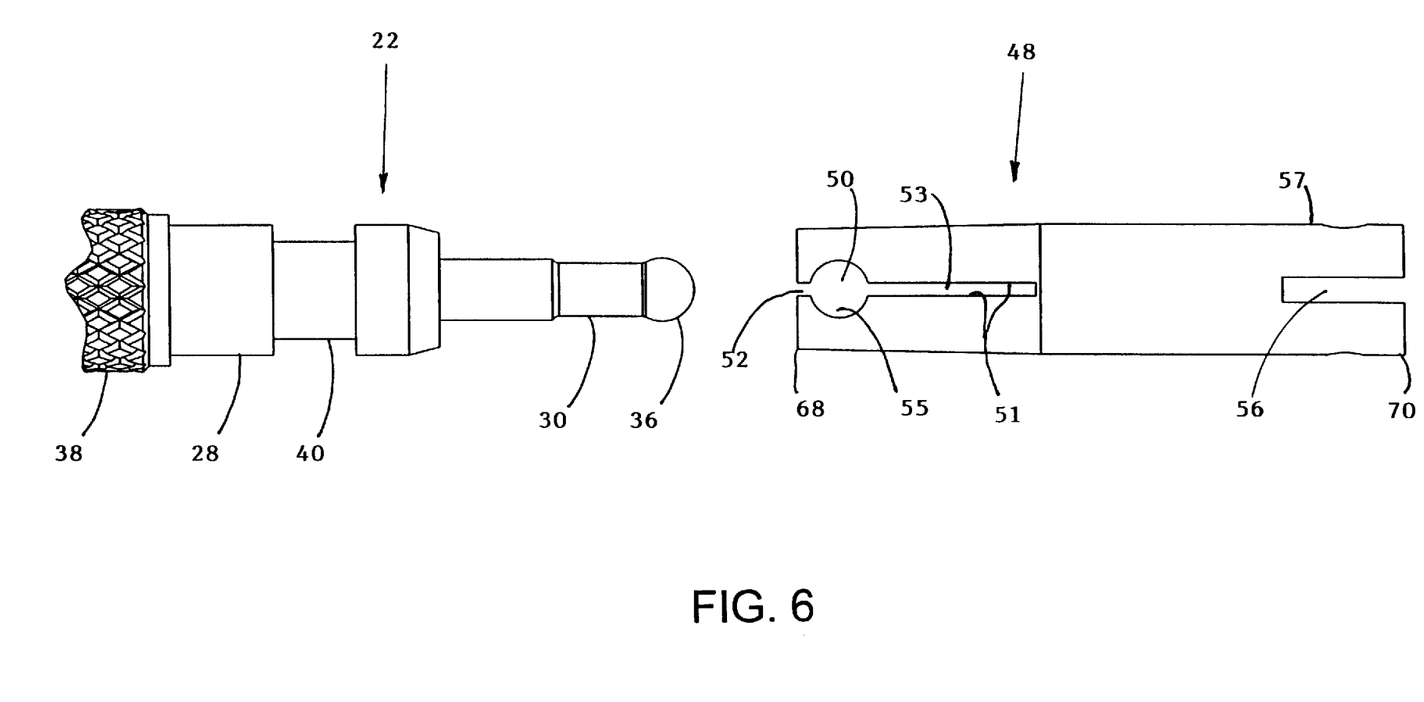
FIG. 6 is an exploded view of the spherical end and socket bushing.
Figure 7:
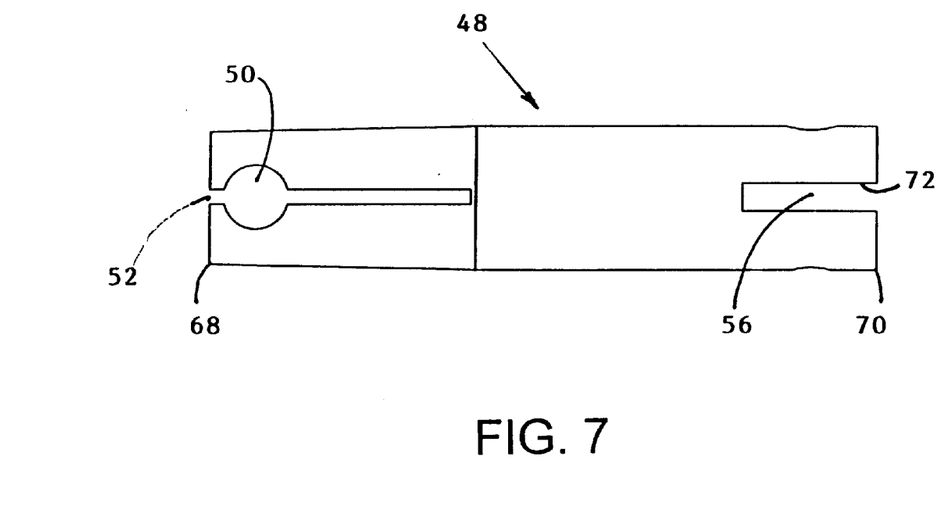
FIG. 7 is an elevational view of the socket bushing.
Figure 8:
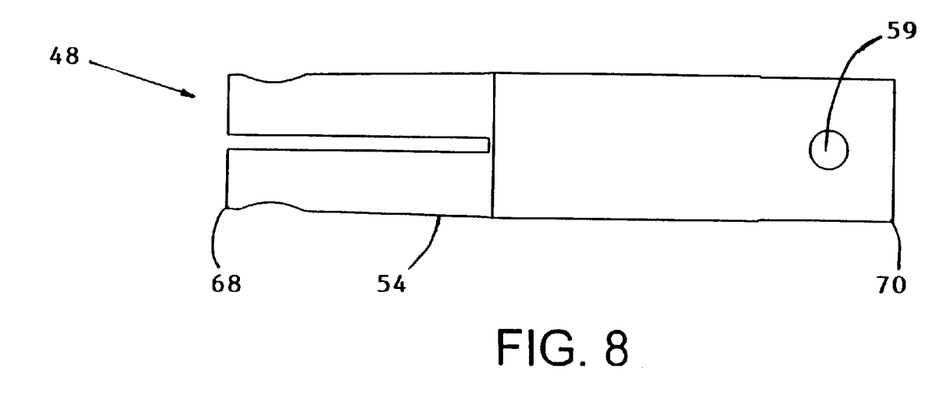
FIG. 8 is a top view of the socket bushing of FIG. 7.
Figure 9:
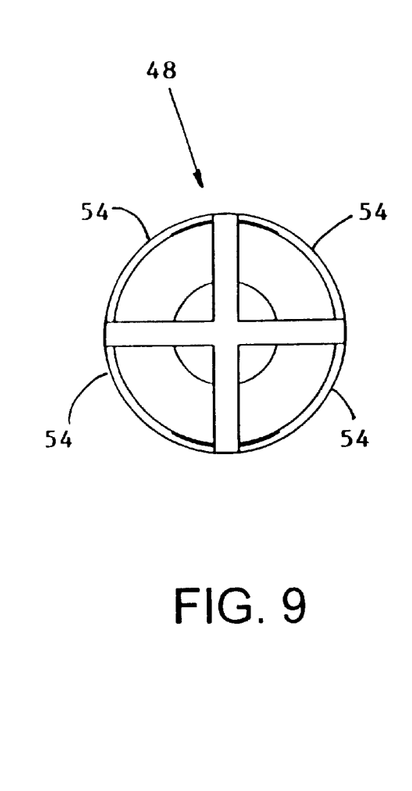
FIG. 9 is a front view of the socket bushing of FIG. 7.

Handle assembly 24 includes a base 45 having a downwardly depending stationary finger handle 42 serving as one section of the handle assembly 24, while the other section is represented by an articulating finger operable, movable thumb handle 44 pivotally mounted to base 45 by a pivot pin 58. The pivot pin 58, being of structure well known to the art, is therefore not detailed in the drawings. As shown in FIGS. 3–4, base 45 includes a housing section 46, having a hollow barrel-shaped bore 47 extending along a longitudinal axis within housing section 46, the bore 47 having a base opening 73 in communication with the environment. FIGS. 3–5 describe the relationship within the housing section 46 wherein a socket bushing 48 is disposed therein, having a flexible end 68 and a linkage end 70. FIGS. 6–9 depict the flexible end 68 having four finger-like resilient prongs 54 extending outwardly. The inner surfaces 51 of prongs 54 defining a passageway 53 extending to a socket opening 52 which is in communication with the bore 47. Further defined by the inner surface 51 of each prong 54 is a recess area 55. The recess areas 55 combiningly and cooperatively define a socket 50 having an inner diameter corresponding essentially to the outer diameter of the spherical end 36. The linkage end 70 of bushing 48 has a pair of generally parallel extending elongate leg sections 57. Leg sections 57 having interior surfaces 72 defining a linkage slot 56 therein. Leg sections 57 being spaced to accommodate a linkage arm 74, to be discussed further in disclosure. Circular apertures 59 are reamed through leg sections 57 in a perpendicular direction to the longitudinal axis of bushing 48. A connector rod 61 transposes through apertures 59 to rotatively contain linkage arm 74. Connector rod 61, being of such conventional design that is well known in the art, is therefore not detailed in drawings.

Thumb handle 44 and base 45 are pivotally connected to each other at their upper portions by a pivot pin 58. Finger handle 42 and thumb handle 44 have convenient grasping elements 60a and 60b of the closed loop design for placement of the fingers and thumb by the surgeon for scissors-like manipulation of the instrument 20. The aforementioned elongate linkage arm 74 interconnects thumb handle 44 to front end assembly 22. Linkage arm 74 having a first end disposed within linkage slot 56, a first linkage hole 76 defined in first end, which upon being aligned with circular apertures 59 of slot 56, engages rotatively with connector rod 61 of bushing 48. Linkage arm 74 further having a second end with a second hole 78 defined therein for rotatively connecting to thumb 44. The connecting method, being of conventional pin means well known to those skilled in the art, is not detailed in the drawings. Finger handle 42 includes a generally semi-circular cutout section 82 and thumb handle includes a generally triangular shaped cutout section, whereby the sections 82 and 86 cooperatively afford linkage arm 74 an area of slidingly movement therein. Extending along one of the elongated edges of linkage arm 74 is a generally straight abutment edge 80. A relatively flat surface is defined along the hypotenuse-like side 84 of thumb handle cutout section 86. Upon being retracted in relationship to finger handle 42, thumb handle 44 freely pivots about base 45 until hypotenuse-like side 84 is juxtaposed to abutment edge 80 of linkage arm 74, thereby disengaging bushing 48 from spherical end 36 of front end assembly 22. It is because of the resiliency of finger-like prongs 54, and because engagement occurs within base 45, that allows the disengagement by the surgeon merely retracting thumb handle 44. When engaged, all actuation of effector mechanism 26, is controlled by pivotal movement of thumb handle 44.

Figure 10:
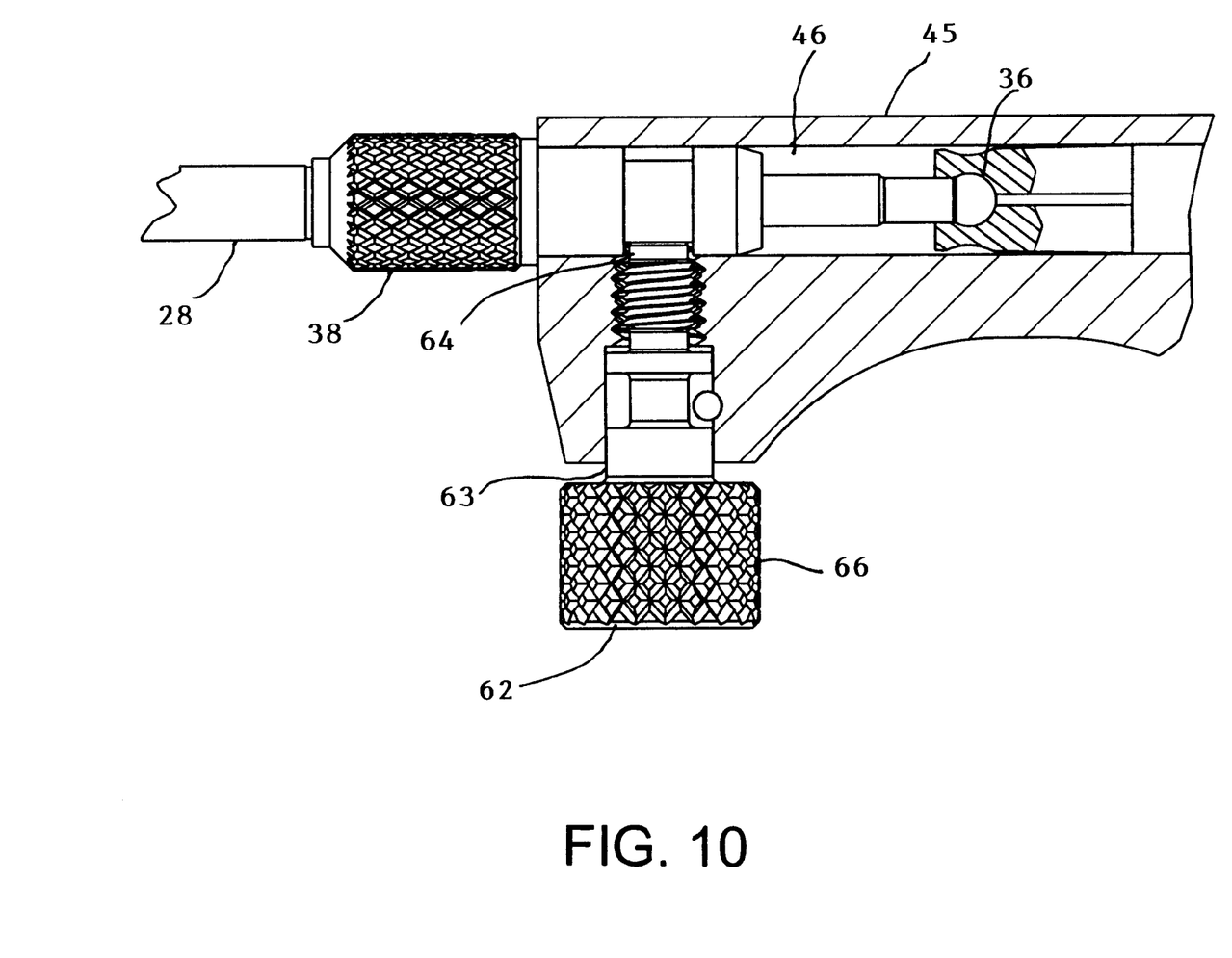
FIG. 10 is a partial cross-section of the locking knob positioned within the undercut section of the sheath.

As shown above, front end assembly 22 is releasably attached to handle assembly 24 by a novel ball and socket arrangement. Spherical end 36 of actuation element 30 is inserted into handle assembly 24, whereby it passes through resilient elongated prongs 54 until it is fully seated within socket 50. To arrest any unwanted movement of front end assembly, either along the longitudinal axis or that of a rotational nature, a threaded locking knob 62 is disposed into a threaded opening 63 in the lower portion of base 45. FIG. 10 depicts locking knob 62 having an elongated threaded section with a contact surface 64 at one and a finger tip grip 66 on the other end. A concentric undercut section 40 is defined in an area of close proximity to proximal end 34 of tubular sheath element 28. The releasable locking-in of front end 22 to handle assembly 24 is accomplished by the user rotating the knob until contact surface 64 is tightenly seated in undercut section 40. To reorient the angle of the end effector mechanism, front end assembly 22 need not be disengaged, only locking knob 62 needs to be loosened.

Whereas many prior art designs utilize a spherical ball seated within a rigid clevis structure (which is generally located in the housing of the pivotal handle), the present invention utilizes a novel ball and socket arrangement, whereby the socket, bushing 48 of the present invention is located in the base portion 45 of the stationary finger handle 42 and the engagement and disengagement of the ball and socket is actuated by pivotable thumb handle 44. The unique finger like prongs 54 allow the user to easily insert spherical end 36 into socket 50.

The assembly of instrument 20 can be performed in the following manner; first holding handle assembly 24 by finger handle 42; then retracting thumb handle 44; then loosening locking knob 62 completely; then inserting spherical end 36 into base 45 of handle assembly 24; then closing and tightening locking knob 64 into undercut 40 of sheath 28 to secure front end assembly 22 in place; and, then closing thumb handle 44 to engage spherical end 36 into socket 50 of socket bushing 48. The instrument 20 is then ready for use. The end effector mechanism 26 may be rotated by loosening locking knob 62, then rotating front end 22 to desired placement of end effectors 26, and then retightening of locking knob 62. To remove front end 22, the thumb handle 44 is retracted, thereby disengaging spherical end 36 from socket 50, then locking knob 62 is loosened and front end 22 is removed.

This design provides a releasable connection that addresses the problems of ease of use, assembly and manufacture.

It is to be understood that the present invention is not limited to the sole embodiment described above, but encompasses any and all embodiments within the scope of the following claims.

LEGEND

20 Endoscopic Instrument
22 Front end Assembly
24 Handle Assembly
26 End Effector Mechanism
28 Tubular Sheath Element
30 Actuation Element
32 Distal end
34 Proximal end
36 Spherical End
38 Knurled grip
40 Concentric Undercut Section in Sheath
42 Stationary Finger Handle
44 Pivotable Thumb Handle
45 Base
46 Housing Section
47 Bore in housing section of Base
48 Socket Bushing
50 Socket
51 Inner surfaces of prongs
52 Socket Opening
53 Passageway defined by inner surface of prongs
54 Prongs 55 Recess area in each prong making up socket
56 Linkage slot in bushing
57 Extending leg sections (2) at actuation end of bushing
58 Pivot Pin
59 Circular apertures in leg sections of bushing
60a Grasping element in Finger Loop
60b Grasping element in Thumb Loop
61 Connector rod
62 Threaded Locking Knob
63 Threaded opening in base for threaded locking knob
64 Contact Surface of locking knob
66 Finger tip grip on locking knob
68 Flexible end of bushing
70 Actuation end of Bushing
72 Interior surface of legs sections
73 Base opening to bore
74 Linkage Arm
76 First linking hole
78 Second linking hole
80 Abutment edge of linkage arm
82 Semi-circular cutout section in finger handle
84 Hypothenuse side
86 Triangular cutout section in thumb handle

I claim:

1. An endoscopic surgical instrument comprising:
    a front end assembly having a distal end and a proximal end, a spherical end slidably connected to said proximal end;
    an operable end effector mechanism attached to said distal end for performing a surgical procedure;
    means for actuating said operable movements of said end effector mechanism;
    a handle assembly having a base, a housing section defined in said base for removably connecting to said spherical end, a stationary finger handle extending downwardly from said base, a thumb handle pivotally mounted to said base;
    means in said base for releasably locking said front end assembly to said handle assembly;
    a socket bushing fixedly disposed within said housing section, said bushing having a flexible end with a plurality of resilient prongs integral with and extending outwardly from said flexible end, each said prong having an inner surface defining a passageway in communication with environment, said inner surfaces each having a recess area defined therein, said recess areas cooperatively combining to define a socket, said socket having an inner diameter corresponding essentially to outer diameter of said spherical end, said spherical end being insertably disposed in a friction fit with said socket therein, said bushing having a linkage end, said linkage end having a pair of generally parallel leg sections, each said leg section having an interior surface defining a linkage slot therein, each said leg having a defined therein a circular aperture being in axial alignment with each other for acceptance of a connector rod; and
    means interconnecting said socket bushing to said thumb handle, whereby said end effector mechanism can be actuated and also said front end asembly can be engaged or disengaged by manipulation of said thumb handle.

2. The instrument according to claim 1, wherein means for connecting said thumb handle to said bushing includes:
    an elongate linkage arm interconnecting between said thumb handle and said bushing;
    said linkage arm having opposing ends, one end having a first linking hole defined therein for disposing into said linkage slot such that said circular apertures are in alignment with first linking hole for rotative connection with said connector rod;
    a second linking hole defined in the other end having means for rotatively connecting to said thumb handle,
    whereby said front end assembly will be mechanically connected and responsive to actuation of said thumb handle such that retraction of said thumb handle will disengage said front end.

3. The instrument according to claim 2, wherein means for rotatively connecting said thumb handle to said second linking hole of said linkage arm comprises:
    a generally straight abutment edge on one side of linkage arm;
    a generally semi-circular cutout section defined in upper portion of said base for slidable travel therein of linkage arm;
    a substantially triangular cutout section in upper portion of said thumb handle for slidable travel therein of linkage arm, a relatively flat surface along hypotenuse side of said linkage arm; and
    a connector pin means for rotatively fastening said second linking hole to said thumb handle,
    whereby surgeon, upon retracting said thumb handle until hypotenuse side is placed in a juxtaposed position relative to said straight abutment edge of said linkage arm, will thereby cause said front end assembly to be disengaged from said handle assembly.

4. The instrument according to claim 3, wherein said front end assembly includes a tubular sheath element, a rod-shaped actuation element cointensive and coaxially slidable within said sheath element, each said element having opposing ends corresponding to distal and proximal ends of said front end assembly, said spherical end integral with proximal end of said actuation element.

5. The instrument according to claim 4, wherein means for releasably locking said front end assembly to said handle assemby comprises:
    a concentric undercut section defined about said sheath in an area of close proximity to said proximal end; and
    a threaded opening in lower section of base, an elongate threaded locking knob disposed in said threaded opening, a knurled finger tip grip at one end of knob for grasping knob to be turned, a contact surface at the other end of knob for seating into said undercut section,
    whereby user rotating said finger tip may urgently seat said contact surface into said undercut section, thereby arresting any slidable or rotational movement of said front end assembly in relation to said handle assembly.

6. The instrument according to claim 5, wherein each said handle includes a hoop-like closed grasping element in each terminating end section, whereby a surgeon's fingers may be inserted during the use of said instrument.

7. The instrument according to claim 6, wherein said front end assembly comprises a knurled grip integral with said sheath in near proximity to said proximal end, for aiding user in grasping said front end assembly.

8. The instrument according to claim 7, wherein said plurality of prongs comprises four prongs equidistantly spaced in relation to each other.

9. The instrument according to claim 8, wherein said base includes a longitudinally extending bore, said bore having at one end a base opening, said housing section fixedly disposed within said bore.

10. An endoscopic surgical instrument having a removable front end assembly, said instrument including:
- a handle assembly having a base, a housing section defined in said base, said housing section including a longitudinal bore, a stationary finger handle extending downwardly from said base, a thumb handle pivotally mounted to said base;
- said front end assembly including a tubular sheath element, a rod-shaped actuation element cointensive and coaxially slidable within said sheath element, each said element having a distal end and a proximal end, a spherical end integral with said proximal end of said actuation element;
- an operable end effector mechanism attached to said distal end of said front end assembly for performing a surgical procedure;
- means for actuating said operable movements of said end effector mechanism;
- means in said base for releasably locking said front end assembly to said handle assembly;
- a socket bushing fixedly disposed within said housing section, said bushing having a flexible end with a plurality of resilient prongs integral with and extending outwardly from said flexible end, each said prong having an inner surface defining a passageway, said passageway being in communication with said bore, said inner surfaces each having a recess area defined therein, said recess areas cooperatively combining to define a socket, said socket having an inner diameter corresponding essentially to outer diameter of said spherical end, said spherical end being insertable through said bore to be disposed in a friction fit within said socket, said bushing having a linkage end, said linkage end having a pair of generally parallel extending leg sections, each said leg section having an interior surface defining a linkage slot therein, each said leg having defined therein a circular aperture being in axial alignment with each other for acceptance of a connector rod;
- an elongate linkage arm interconnecting between said thumb handle and said bushing;
- said linkage arm having a first end and a second end, said first end having a first linking hole disposed within said linkage slot such that said circular apertures in said legs are in alignment with said first linking hole for connection by said connector rod;
- a staight abutment edge on one side of said linkage arm;
- means for connecting said second end of said linkage arm to said thumb handle,
- whereby said end effector mechanism can be actuated and said front end assembly can be engaged or disengaged by simple manipulation of said thumb handle by surgeon.

11. The instrument according to claim 10, wherein means for releasably locking said first end assembly to said base portion comprises:
- a concentric undercut section defined about said sheath in an area of close proximity to said proximal end; and
- a threaded opening in lower section of base, an elongate threaded locking knob disposed in said threaded opening, a knurled finger tip grip at one end of knob for grasping knob, a contact surface at the other end of knob for seating into said undercut section,
- whereby user rotating said finger tip may urgently seat said contact surface into said undercut section, thereby arresting any slidable or rotational movement of said front end assembly in relationship to said handle assembly.

12. An instrument according to claim 11, wherein said base comprises a generally semi-circular cutout section in upper portion therewithin, for slidable travel of said linkage arm therein.

13. An instrument according to claim 12, wherein said thumb handle comprises:
- a generally triangular cutout section in upper portion thereof for slidable travel of said linkage arm therein; and
- a flat surface along hypotenuse side of said triangular cutout section for flush contact with straight abutment edge side of said linkage arm,
- whereby surgeon retracts said thumb handle until said hypotenuse side is in a juxtaposed releationship to said straight abutment edge of said linkage arm, thereby causing said front end assembly to be disengaged from said handle assembly.

14. The instrument according to claim 13, wherein each said handle includes a loop-like closed grasping element in each terminating end section, whereby a surgeon's fingers may be inserted during the use of said instrument.

15. The instrument according to claim 6, wherein said front end assembly comprises a knurled grip integral with said sheath in near proximity to said proximal end, for aiding user in grasping said front end assembly.

16. The instrument according to claim 15, wherein said plurality of prongs comprises four said prongs equidistantly spaced in relationship to each other.

17. An endoscopic surgical instrument having a removable front end assembly, the instrument including:
- (a) a manually controllable handle assembly having:
  - (i) a base, a housing section having a bore defined in upper section of said base therein,
  - (ii) a downwardly depending stationary finger handle extending from said base serving as one section of said base,
  - (iii) a thumb handle pivotally mounted to said base serving as another section of said base,
  - (iv) said thumb handle having a generally triangular shaped cutout section defined in its upper portion, hypotenuse side of said cutout section having a generally flat surface,
  - (v) said base having a substantially semi-circular cutout section defined in its upper portion,
  - (vi) a closed grasping element in terminating end section of each said handle, whereby fingers of surgeon may be inserted during use of the instrument,
  - (vii) a threaded opening in lower portion of said base;
- (b) an elongate socket bushing disposed within said housing section comprising:
  - (i) said bushing having a flexible end and an opposing linkage end,
  - (ii) four elongate resilient prongs comprising said flexible end of said socket bushing, each said prong having an inner surface defining a passageway, each said inner surface having a recess area therein,
  - (iii) a spherical socket defined by cooperative combination of said recess areas of said prongs,
  - (iv) an opening to said socket defined by said prongs,
  - (v) a pair of substantially parallel legs extending from said linkage end, the interior surfaces of said legs defining a longitudinal slot therein, each of said legs having circular apertures defined therein, apertures in axial alignment to accept a connector rod;
(c) a front end assembly being releasably attached to and extending from said handle assembly, said front end assembly including:
  (i) a tubular sheath element extending from said handle assembly,
  (ii) an actuation element cointensive and coaxially slidable within said tubular sheath member,
  (iii) each said element having a distal end and a proximal end,
  (iv) means for attaching to the distal end an operable end effector mechanism for performing surgical procedures,
  (v) a spherical end integral with the proximal end of said actuation element, for engagement within said socket disposed in said bushing,
  (vi) a concentic undercut section defined in said sheath member in close proximity to the proximal end of said sheath,
  (vii) a knurled grip integral with said tubular sheath for grasping said sheath for rotation of said front end assembly to a multitude of orientation angles;
(d) an elongate threaded locking knob rotatably mounted in said threaded opening of said base, said locking knob including:
  (i) at one end a finger tip grip having a knurled exterior for easy grasping,
  (ii) at the other end a contact surface for engaging with said undercut section of said sheath element for releasably arresting said front end assembly to said handle assembly; and
(e) means for actuating the end effector mechanism or for disengaging said front end assembly from said handle assembly, said means comprising:
  (i) an elongate linkage arm having a first end cooperatively disposed within said linkage slot of said socket bushing, a first linking hole defined therein for alignment with said circular apertures such that said linkage arm can be rotatively fastened to said connector rod, a second end having a second linking hole defined therein for connecting to said thumb loop handle, a straight abutment edge extending along one side of said linkage arm, whereby said linkage arm may slidingly move through said triangular and semi-cicular cutout sections until said abutment edge is juxtaposed against said hypotenuse side of said triagular cutout of said thumb handle, whereby said front end assembly can be disengaged from said handle assembly by surgeon pivotally retracting said thumb handle and end effectors actuated by the surgeon manipulating said pivoting thumb handle.

* * * * *